United States Patent

Dyckman et al.

Patent Number: 5,672,774
Date of Patent: Sep. 30, 1997

[54] PHENOL TAR PROCESSING METHOD

[75] Inventors: Arkady S. Dyckman; Vadim P. Boyarsky, both of St. Petersburg; Alexander S. Malinovskii, Novokuibishevsk; Yurii I. Petrov, Novokuibishevsk; Leontii M. Krasnov, Novokuibishevsk; Andrey V. Zinenkov, St. Pertersburg; Boris I. Gorovits, St. Petersburg; Sergey N. Chernukhim, St. Novokuibishevsk; Anatoly D. Sorokin, Novokuibishevsk, all of Russian Federation; John W. Fulmer, Mt. Vernon, Ind.

[73] Assignee: General Electric Company, Pittsfield, Mass.

[21] Appl. No.: 547,252

[22] Filed: Oct. 24, 1995

[51] Int. Cl.⁶ .................................. C07C 37/68
[52] U.S. Cl. ............................ 568/749; 568/750
[58] Field of Search .......................... 568/749, 750

[56] References Cited

U.S. PATENT DOCUMENTS

| | | |
|---|---|---|
| 2,715,145 | 8/1955 | Hawley et al. . |
| 3,850,996 | 11/1974 | Nixon . |
| 3,968,171 | 7/1976 | Burkholder et al. ............ 568/749 |
| 4,016,213 | 4/1977 | Yeh et al. . |
| 4,173,487 | 11/1979 | Wu et al. . |
| 4,207,264 | 6/1980 | Anderson et al. . |
| 4,310,712 | 1/1982 | Langley . |
| 4,358,618 | 11/1982 | Sifniades et al. . |
| 4,559,110 | 12/1985 | Swearingen . |
| 4,827,050 | 5/1989 | Peter et al. ............... 568/749 X |
| 4,929,786 | 5/1990 | Himmele et al. . |
| 5,015,786 | 5/1991 | Araki et al. . |
| 5,017,729 | 5/1991 | Fukuhara et al. . |
| 5,144,094 | 9/1992 | Richmond et al. . |
| 5,254,751 | 10/1993 | Zakoshansky . |
| 5,371,305 | 12/1994 | Hood . |
| 5,504,251 | 4/1996 | Dyckman et al. ............ 568/749 X |
| 5,510,543 | 4/1996 | Fulmer et al. ............... 568/749 X |

FOREIGN PATENT DOCUMENTS 7080-332  11/1980  Japan .

OTHER PUBLICATIONS

"Side Reactions in the Phenol/Acetone Process. A Kinetic Study", Ind. Eng. Chem. Res. 1988, 27, 4–7, Pier Luigi Beltrame, et al.

*Primary Examiner*—Paul F. Shaver

[57] ABSTRACT

Valuable products are recovered from phenol tar by thermocracking under controlled conditions in the presence of polyphosphoric acid. Bisphenol A tars can be optionally cracked under these conditions mixed with the phenol tar and enhanced yields obtained.

10 Claims, No Drawings

PHENOL TAR PROCESSING METHOD

This invention relates to petrochemical technology, namely to phenol and acetone production by the cumene method.

In the phenol and acetone product of the process, referred to as the cumene method, high-boiling byproducts are formed and are referred to, commonly, as phenol tar. Phenol tar is a complex material consisting of many components including phenol, acetophenone (AP), $\alpha$, $\alpha$-dimethylbenzylalcohol (DMBA), dimers of $\alpha$-methylstyrene (AMSD), o, p-cumylphenols (CP), unidentified components, and a small amount of salts (mainly $Na_2SO_4$). The exact phenol tar composition is dependent on the specific phenol production technology and can vary over a wide range.

| Phenol Tar | wt % |
|---|---|
| Phenol | 5–40 |
| Acetophenone (AP) | 5–30 |
| Dimethylbenzyl alcohol (DMBA) | 1–15 |
| alpha methylstyrene dimers (AMSD) | 3–35 |
| o, p-cumylphenols (CP) | 10–50 |
| Heavy components | 20–65 |

Until recently phenol tar was completely useless. Large amounts of it have been used as fuel, but this has caused ecological problems because of ash formation and difficulties in burning the highly condensed aromatic compounds. So a process for phenol tar which would recover a maximum amount of useful products such as cumene, phenol, and $\alpha$-methylstyrene and reduce the amount of tar disposed of by burning would have great value.

There was previously proposed a method comprising distilling phenol tar to remove AP and phenol, then pyrolyzing the phenol tar, from which AP and phenol have been removed, at 200°–400° C. with an acid catalyst (the examples use sulfuric acid) and then distilling the pyrolysis product to remove the AP and phenol formed in pyrolysis from the other valuable products to prevent further reaction by AP and phenol which would form more tars. According to this method the phenol tar must be pre-distilled to remove the free phenol and acetophenone from it, or else condensation reactions occur during the cracking operation to form additional tars and negating recovery of valuable products.

Disadvantages of this method are the necessity of this additional initial distillation step and little or no improvement in total valuable products yield (TVPY, which is the sum of phenol, AMS and cumene yields) as a function of sulfuric acid catalyst concentration, as shown in Table 1.

The sulfuric acid serves only to reduce thermocracker temperature to save energy usage. Further, sulfuric acid, at these concentrations and at these temperatures, gives an extremely corrosive environment which attacks the distillation equipment even if made from stainless steel requiring either exotic alloys or glass linings.

TABLE 1

| Phenol tar thermocracking process data: | | | | |
|---|---|---|---|---|
| | 1 | 2 | 3 | 4 |
| AMSD, wt % | 6.1* | — | — | — |
| CP, wt % | 68.5* | — | — | — |
| Heavy components, wt % | 25.4* | — | — | — |
| Process temperature, °C. | — | 405 | 263 | 360 |

TABLE 1-continued

| Phenol tar thermocracking process data: | | | | |
|---|---|---|---|---|
| | 1 | 2 | 3 | 4 |
| $H_2SO_4$ concentration, wt % | — | — | 1 | 0.25 |
| Thermocracker, Distillate/Feed, wt % | — | 76.4 | 69.2 | 70.3 |
| Valuable products in distillate conc., weight % | — | 91.6 | 99.6 | 81.0 |
| TVPY, kg/t of tar | — | 699.8* | 689.0* | 569.6* |

Data from U.S. Pat. No. 2715145 (1955) incorporated herein by reference
*Calculated from the data in examples 1–4 of the patent. AP and phenol removed from feed by distillation before cracking.

Another known prototype method is the continuous thermocracking of phenol tar in a column-type reactor at 275°–420° C. Feed tar is fed into the middle of the column and the resulting distillate is taken off from the top of the column and partially directed back to the column as a reflux (reflux ratio (L/D) about 8). Bottom product is taken off continuously. Process operation pressure is 2.5 atmospheres absolute. The phenol tar composition used as a feed is presented in Table 2.

TABLE 2

| Phenol tar composition | |
|---|---|
| Component | Contents, % mas. |
| Phenol | 15.4 |
| AP | 9.3 |
| DMBA | 9.1 |
| CP | 40.9 |
| Heavy components | 25.3 |

Data from U.S. Pat. No. 3,850,996 (1974) incorporated herein by reference.

The above mentioned prototype results in a distillate containing valuable products: cumene, phenol, and AMS. Most AP, coming into the thermocracker with the feed remains in the pot, where it is converted by condensation reactions with itself and phenol into heavy products and directed to incineration. Although the patent teaches a high level of recovery of TVPY, efforts to reproduce the results in the single patent example show a recovery of less than half of what is taught.

The difficulty in reproducing the performance of this prototype as taught in the patent is caused by the fact that during the cracking operation the AP component reacts with the valuable free phenol component present in the tar feed stream forming highboiling tarry by-products. Also in this prototype the TVPY obtained is very strongly dependent on phenol tar composition. (phenol, CP, AMS dimers and DMBA content) and does not provide the broad range of effectiveness as the present process with tar feeds of greatly differing compositions, in particular free phenol content.

Another disadvantage of this method is the significant amount of bottom residue, which is incinerated and results in a low level of recovery of valuable products.

A comparison of the feed streams shown in Tables 1, 2 and 3 illustrates the need for the more effective thermocracking process of the present invention. Whereas the CP level in the phenol tar was 68.5 in the 1950's, by the 1970's it dropped to 40.9% and now in the 1990's it is at 15.6%. This change in composition of the tar feed stream results from more effective upstream separation techniques and more effective catalysts which reduce the lights ends of the tar stream and raise the level of heavy components. CP is one of the components in the tar feed stream that yields the greatest quantity of TVPY. Although the present thermocracking process is highly effective with a rich tar feed stream such as in Table 1, such rich feeds are no longer available in modern phenol from cumene plants. Thus, the key to an economically attractive tar cracking process is to recover TVPY from tar feed streams with a substantial proportion of heavy components, e.g. over 40% by weight compared to about 25% by weight in old processes.

The present invention improves TVPY, increases the degree of phenol tar processing, and reduces the amount of heavy by-products.

These results are obtained by carrying out the thermocracking process under controlled acidic conditions in a column-type reactor with a pot temperature of from 200° to 360° C. and a pressure of from 0.1 to 5 atmospheres absolute and taking off the distillate fraction which contains the desired products: phenol cumene, and AMS, and a relatively small amount of acetophenone. The resulting fraction from the thermocracker can be directed either to an existing phenol and hydrocarbons separation system, or to a specially designed one to separate some of the components (e.g. AP) of this stream.

Surprisingly, under the conditions of the process of the present invention, the AP and phenol do not condense to form tars as in the processes of the prior art which reduced the level of valuable products recovered by these processes. Further, the present process is more energy and capital efficient since a pre-pyrolysis distillation is avoided. The phenol tar thermocracking process employs 0.1–1% by weight of phosphoric acid pre-heated to 50°–180° C. as a catalyst. When commercial phosphoric acid is used (85 weight percent assay) the amount added should corrected to a 100% by weight basis. Any concentration of phosphoric acid may be used but lower than about 85% by weight increases the water level undesirably.

A noticeable distinguishing characteristic of the present invention is the use of the 0.1–1 weight % additive of phosphoric acid pre-heated to 50°–180° C. This procedure increases TVPY by 120–250 kg per ton of phenol tar.

This improvement in tar cracking efficiency can be explained by the in-situ formation of strong acids such as pyrophosphoric acid (stronger than phosphoric acid itself), which possess enhanced catalytic activity. Thus, in the hot thermocracking environment, pyrophosphoric acid and the higher condensed analogs of phosphoric acid form via dehydration and condensation reactions as shown below:

  (1)

  (2)

The formation of polyphosphoric acid esters by reactions of such acids with phenol tar components is also possible. The effectiveness of the above catalyst system can be further explained by virtue of the fact that the polyphosphoric acids are non-volatile and remain intimately mixed within the tar mixture during the high temperature thermocracking process. Other catalysts such as sulfuric acid vaporize at these temperatures, quickly leave the cracking zone after addition to the feed stream, and thus are much less effective as cracking catalysts. Another benefit is that the polyphosphoric acids are not as corrosive as sulfuric acid when in contact with the materials of construction, such as stainless steel, typically used in phenol production plants.

Processing at lower than the minimum pot temperature (<200° C.) significantly decreases TVPY, as the influence of catalyst added is reduced. Exceeding the maximum pot temperature (>360° C.) leads to a strong rise in the bottom liquid viscosity and the fouling of pipes. One can observe a similar effect from a catalyst concentration >1.0%. Addition of <0.1 weight % of phosphoric acid does not effectively catalyze the cracking process, and in some cases can even reduce TVPY in comparison with no phosphoric acid additive. Overheating of the phosphoric acid (>180° C.) will lead to bottom product viscosity rise and heating the phosphoric acid to a temperature <50° C. won't provide high process efficiency. Carrying out the process at a pressure lower than 0.1 atmospheres absolute is not as effective since an elevated AMS dimers concentration in the distillate results instead of decomposition of the dimers into AMS. Bottom residue viscosity is also increased. A processing pressure higher than 5 atmospheres absolute provides high bottom residue viscosity causing handling problems and potential for equipment fouling.

It is preferred to maintain the residence time in the pot between about 4 and abut 30 hours, more preferably between about 5 and about 20 hours, and still more preferably between 5 and about 10 hours.

Addition of 10–90% of bisphenol tar (Bisphenol A, obtained by phenol and acetone condensation, distillation bottom product) to the phenol tar can give further benefits beyond the preheated phosphoric acid addition alone.

Typically, the bisphenol-A tar comprises the following main components (percent by weight);

| Component | Amount |
|---|---|
| Phenol | 5–20 wt % |
| p, p-bisphenol-A | 15–40 |
| o, p-bisphenol-A | 5–10 |
| IPP dimer | 3–8 |
| Chroman | 5–15 |
| BPX (trimer) | 7–15 |
| Heavy Tar | The rest to total 100% |

IPP means isopropenyl phenol

BPX is a molecule with a molecular weight of 362 and is fully described in pending application Ser. No. 08/401,732, filed Mar. 9, 1995, which is expressly incorporated herein by reference.

The efficiency of the present process is illustrated by following examples. The composition of the phenol tar feed stream used in these examples is set forth in Table 3. The composition of the bisphenol-A (BPA) tar feed stream used in Examples 5 and 6 is set forth in Table 4.

TABLE 3

Phenol tar composition

| Component | Contents, % mas. |
|---|---|
| Light components | <0.01 |
| Cumene | 0.02 |
| AMS | 0.1 |
| Phebol | 16.7 |
| AP | 15.6 |
| DMBA | 5.5 |
| AMS dimers | 5.8 |
| CP | 15.4 |
| Heavy components | 40.9 |

TABLE 4

BPA tar composition

| Component | Weight Percent |
| --- | --- |
| Phenol | 6.6 |
| Acetophenone | — |
| o, p-Cumylphenol | — |
| p, p-bisphenol-A and o, p-bisphenol-A | 36.2 |
| IPP Dimers | 4.1 |
| Chroman | 10.2 |
| (BPX) (Trimer) | 14.2 |
| Tars | 28.7 |

EXAMPLE 1.

Phenol tar processing was carried out using the column type reactor of the present invention. Temperature in the pot of the column was 315° C., pressure 3.0 At abs. Feed—phenol tar of the composition presented in Table 3. Column distillate is partially used as a reflux with a reflux ratio 2.0. 0.18% of phosphoric acid preheated to 150° C. was added to the feed inputted into the middle of column. Experimental results are presented in Table 5 (Example 1).

EXAMPLE 2.

Phenol tar processing was carried out the same as in Example 1, but phosphoric acid concentration was 1.0%, phosphoric acid preheat temperature is 180° C. bottom temperature was 200° C., operation pressure was 0.1 Atmospheres absolute. Experimental results are presented in Table 5 (Example 2).

EXAMPLE 3.

Phenol tar processing was carried out the same as in Example 1, but phosphoric acid concentration was 0.1%, phosphoric acid preheat temperature is 50° C. Experimental results are presented in Table 5 (Example 3).

EXAMPLE 4.

Phenol tar processing was carried out the same as in Example 1, but phosphoric acid was preheated to 180° C., bottom temperature is 360° C., operation pressure was 5 Atmospheres absolute. Experimental results are presented in Table 5 (Example 4).

EXAMPLE 5.

Phenol tar processing was carried out the same as in Example 1, but 10% of BPA tar was added to the feed. Experimental results are presented in Table 5 (Example 5).

EXAMPLE 6.

Phenol tar processing was carried out the same as in Example 1, but 90% of BPA tar was added to the feed. Experimental results are presented in Table 5 (Example 6).

EXAMPLE 7.

Comparative phenol tar processing was carried out the same as in Example 1, but without phosphoric acid additives, and a reflux ratio of 8. Experimental results are presented in Table 5 (Example 7).

TABLE 5

Phenol tar thermocracking process indices

| Example | 1 | 2 | 3 | 4 | 5 | 6 | 7 |
| --- | --- | --- | --- | --- | --- | --- | --- |
| Pot temperature, °C. | 315 | 200 | 315 | 360 | 315 | 315 | 315 |
| $H_3PO_4$ preheating temperature, °C. | 150 | 180 | 50 | 180 | 150 | 150 | — |
| Pressure, At abs. | 3.0 | 0.1 | 3.0 | 5.0 | 3.0 | 3.0 | 3.0 |
| $H_3PO_4$ concentration, % | 0.18 | 1.0 | 0.1 | 0.1 | 0.18 | 0.18 | 0 |
| *BPA tar additive % | — | — | — | — | 10 | 90 | — |
| TVPY, kg/t | 525 | 350 | 494 | 539 | 548** | 554** | 275 |
| Including, kg/t: | | | | | | | |
| Phenol | 194 | 187 | 218 | 223 | 211 | 210 | 105 |
| AMS | 240 | 158 | 186 | 194 | 248 | 251 | 99 |
| Cumene | 91 | 5 | 90 | 122 | 89 | 93 | 71 |

*BPA tar is the bottom liquid from Bisphenol A process after Bisphenol A distillation.
**Phenol tar is the only contributor. Pure BPA tar at such conditions provides 300 kg of phenol per 1 ton of tar. Phenol formed from this BPA tar has been subtracted from the total phenol amount.

We claim:

1. A method for recovery of valuable products from phenol tar, obtained from a phenol and acetone manufacturing process, comprising charging a phenol tar into a thermocracking process column-type reactor, heating the bottoms of the reactor to a temperature of from 200° C. to 360° C., maintaining the reactor at a pressure of from 0.1 to 5 atmospheres absolute and cracking the tar in the presence of 0.1 to 1.0 weight percent of phosphoric acid preferably 0.1–0.2 wt %, preheated to 50° C.–180° C., with such phosphoric acid being added whereby it dehydrates and polymerizes to its non-volatile polyphosphoric acid analogs.

2. A method of claim 1, wherein bottom residue of a Bisphenol A distillation is added to the feed tar to give a tar mixture of from 10% to 90% by weight bottom residue and from 90% to 10% by weight phenol tar.

3. A method of claim 1 wherein the reactor is under reflux.

4. A method of claim 3 wherein the reflux ratio (L/D) is about 2/1 or less, and preferably less than 1/1.

5. A method of claim 1 wherein the pressure is from 0.1 to about 3.0 atmospheres absolute.

6. A method of claim 1 wherein the bottoms of the reactor are heated to a temperature of from about 300° C. to about 330° C.

7. A method of claim 1 wherein the amount of phosphoric acid is from 0.1 weight percent to about 0.2 weight percent.

8. A method of claim 1 wherein the tar has a residence time in the bottom of the reactor of from about 4 to about 30 hours.

9. A method for recovery of valuable products from phenol tar, obtained from a phenol and acetone manufacturing process, comprising charging a phenol tar into a thermocracking process column-type reactor, heating the bottoms of the reactor to a temperature of from about 300° C. to about 330° C., maintaining the reactor at a pressure of from 0.1 to about 3.0 atmospheres absolute and cracking the tar in the presence of 0.1 to about 0.2 weight percent of phosphoric acid preheated to 50° C. to 180° C., with such phosphoric acid being added whereby it dehydrates and polymerizes to its non-volatile polyphosphoric acid analogs.

10. A method of claim 9 wherein the tar has a residence time in the bottom of the reactor of from 5 to about 10 hours.

* * * * *